(12) United States Patent
Bettuchi

(10) Patent No.: US 8,025,641 B2
(45) Date of Patent: Sep. 27, 2011

(54) POWERED VARIABLE SEAL DIAMETER TROCAR EMPLOYING A WINEPRESS MECHANISM

(75) Inventor: Michael Bettuchi, Middletown, CT (US)

(73) Assignee: Tyco Healthcare Group LP, New Haven, CT (US)

( * ) Notice: Subject to any disclaimer, the term of this patent is extended or adjusted under 35 U.S.C. 154(b) by 0 days.

(21) Appl. No.: 12/957,573

(22) Filed: Dec. 1, 2010

(65) Prior Publication Data

US 2011/0152777 A1   Jun. 23, 2011

Related U.S. Application Data

(60) Provisional application No. 61/287,813, filed on Dec. 18, 2009.

(51) Int. Cl.
*A61B 17/34* (2006.01)
(52) U.S. Cl. ......... 604/167.03; 604/167.01; 604/167.04; 604/256
(58) Field of Classification Search .......... 604/164.01–164.04, 164.07, 164.12, 604/165.04, 167.01–167.03, 256, 264; 251/149.1–149.3, 4
See application file for complete search history.

(56) References Cited

U.S. PATENT DOCUMENTS

| | | | |
|---|---|---|---|
| 3,197,173 A * | 7/1965 | Taubenheim | ............ 251/6 |
| 4,978,341 A | 12/1990 | Niederhauser | |
| 5,030,206 A | 7/1991 | Lander | |
| 5,053,016 A | 10/1991 | Lander | |
| 5,059,186 A | 10/1991 | Yammamoto et al. | |
| 5,108,380 A | 4/1992 | Herlitze et al. | |
| 5,197,955 A | 3/1993 | Stephens | |
| 5,207,409 A * | 5/1993 | Riikonen | ............ 251/7 |
| 5,263,944 A | 11/1993 | Vidal et al. | |
| 5,304,143 A | 4/1994 | Green et al. | |
| 5,308,336 A | 5/1994 | Hart et al. | |
| 5,334,164 A * | 8/1994 | Guy et al. | ............ 604/248 |
| 5,342,315 A | 8/1994 | Rowe | |
| 5,350,364 A * | 9/1994 | Stephens et al. | ..... 604/167.06 |
| 5,366,445 A | 11/1994 | Haber | |
| 5,385,552 A | 1/1995 | Haber | |
| 5,385,553 A | 1/1995 | Hart | |
| 5,389,081 A | 2/1995 | Castro | |
| 5,391,153 A | 2/1995 | Haber | |
| 5,391,154 A | 2/1995 | Young | |
| 5,397,314 A | 3/1995 | Farley | |

(Continued)

OTHER PUBLICATIONS

European Search Report EP 08 25 1792 dated Sep. 1, 2008.

(Continued)

*Primary Examiner* — Nicholas D Lucchesi
*Assistant Examiner* — Quynh-Nhu H Vu

(57) ABSTRACT

A surgical access apparatus includes an access member having a longitudinal passageway providing access to a tissue site. An elongated seal member mounted to the access member has an orifice with a variable inner dimension. The elongated seal member establishes a sealing relation about an instrument and is associated with a powered adjustment mechanism for adjusting the variable inner dimension of the orifice. The powered adjustment mechanism includes trailing and leading hubs longitudinally spaced and adapted for relative rotation about an axis defined by the access member. A plurality of spokes extends between the hubs and defines first and second minimum internal dimensions when in first and second conditions respectively upon relative rotation of the hubs. The spokes are arranged about the elongated seal member to adjust the variable inner dimension of the orifice upon relative rotation of the hubs. A powered motion generator effects relative rotation between the hubs.

10 Claims, 3 Drawing Sheets

U.S. PATENT DOCUMENTS

| | | |
|---|---|---|
| 5,407,433 A | 4/1995 | Loomas |
| 5,411,483 A | 5/1995 | Loomas |
| 5,417,705 A | 5/1995 | Haber |
| 5,429,609 A | 7/1995 | Yoon |
| 5,441,486 A | 8/1995 | Yoon |
| 5,496,280 A | 3/1996 | Vandenbroek |
| 5,538,509 A | 7/1996 | Dunlap |
| 5,545,142 A | 8/1996 | Stephens |
| 5,549,565 A | 8/1996 | Ryan |
| 5,603,702 A | 2/1997 | Smith |
| 5,634,908 A | 6/1997 | Loomas |
| 5,657,963 A | 8/1997 | Hinchliffe |
| 5,685,854 A | 11/1997 | Green |
| 5,709,664 A | 1/1998 | Vandenbroek |
| 5,720,759 A | 2/1998 | Green |
| 5,792,113 A | 8/1998 | Kramer |
| 5,814,026 A | 9/1998 | Yoon |
| 5,895,377 A | 4/1999 | Smith |
| 5,913,847 A | 6/1999 | Yoon |
| 5,989,233 A | 11/1999 | Yoon |
| RE36,702 E | 5/2000 | Green |
| 6,083,203 A | 7/2000 | Yoon |
| 6,099,505 A | 8/2000 | Ryan |
| 6,171,299 B1 | 1/2001 | Bonutti |
| 6,358,266 B1 | 3/2002 | Bonutti |
| 6,482,181 B1 | 11/2002 | Racenet |
| 6,551,282 B1 | 4/2003 | Exline |
| 6,595,946 B1 | 7/2003 | Pasqualucci |
| 6,702,787 B2 | 3/2004 | Racenet |
| 6,811,546 B1 | 11/2004 | Callas |
| 6,923,783 B2 | 8/2005 | Pasqualucci |
| 6,942,671 B1 | 9/2005 | Smith |
| 7,011,314 B2 | 3/2006 | McFarlane |
| 7,025,747 B2 | 4/2006 | Smith |
| 7,083,626 B2 | 8/2006 | Hart |
| 7,169,130 B2 | 1/2007 | Exline |
| 7,244,244 B2 | 7/2007 | Racenet |
| 7,276,075 B1 | 10/2007 | Callas |
| 7,390,317 B2 | 6/2008 | Taylor |
| 7,438,702 B2 | 10/2008 | Hart |
| 7,470,255 B2 | 12/2008 | Stearns |
| 2005/0092944 A1* | 5/2005 | Patterson .................. 251/4 |
| 2006/0071432 A1 | 4/2006 | Staudner |
| 2009/0312697 A1* | 12/2009 | Zemlock ................ 604/95.04 |

OTHER PUBLICATIONS

US 7,282,043, 10/2007, Racenet (withdrawn)

* cited by examiner

POWERED VARIABLE SEAL DIAMETER TROCAR EMPLOYING A WINEPRESS MECHANISM

CROSS REFERENCE TO RELATED APPLICATION

The present application claims the benefit of and priority to U.S. Provisional Application Ser. No. 61/287,813 filed on Dec. 18, 2009, the entire contents of which are incorporated herein by reference.

BACKGROUND

1. Technical Field

The present disclosure relates generally to a surgical access apparatus employing a system for maintaining a fluid-tight seal across a passageway for surgical instruments. In particular, the disclosure relates to a portal apparatus employing a variable diameter winepress seal in communication with a power source for accommodating instruments of various sizes.

2. Background of Related Art

Surgical procedures such as laparoscopic, arthroscopic, and endoscopic procedures in general are termed minimally invasive at least in part because the incision required is relatively small, perhaps one inch in length or less. Small incisions are preferred because they are inherently less traumatic to the surrounding body tissue. Also, small incisions subject internal organs to a limited exposure to the contaminants in the outside atmosphere. Thus, small incisions enable shorter hospital stays and faster recoveries with less pain and scarring than is common with the larger incisions required for conventional surgery.

Endoscopic surgery is possible due in part to the availability of instruments designed specifically for this purpose. A trocar assembly, for example, may include a sharp trocar or obturator for creating a small incision, and a cannula assembly for providing a conduit through the incision once the obturator has been removed. A cannula is an elongated tube, e.g., 2 mm to 15 mm in diameter, which may be configured to have a distal or leading end inserted into an internal body cavity adjacent an operative site. The body cavity is often inflated with an insufflation gas, carbon dioxide, for example, to separate the body wall from vital organs. This provides a space where a surgeon may introduce viewing equipment or maneuver tools into position without damaging surrounding tissue. Various other instruments may then be inserted and withdrawn through the cannula for access to the working space and operative site. In order to fit through a cannula and enable a surgeon to manipulate tissue far removed from the incision, instruments adapted for endoscopic surgery typically include a long and narrow cylindrical shaft. The exact size and shape of the instrument shaft may vary for the several instruments commonly required for a single procedure.

Endoscopic procedures generally require that any instrumentation inserted into the patient's body be sealed, e.g., provisions must be made to ensure insufflation gas does not escape the body through the cannula. Furthermore, a seal acts to prevent contamination of the body cavity by the outside environment. In the absence of such a fluid-tight seal, many of the attendant advantages of minimally invasive surgery are lost. In order to maintain a seal at all times, e.g., before, during and after the introduction of an instrument into the cannula, a dual seal system is commonly employed. A first seal is normally biased to a closed condition to seal the conduit in the absence of an instrument. Because the first seal may be defeated upon the introduction of an instrument, a second seal may be positioned to establish a sealing relation with the shaft of the instrument before the first seal is compromised.

The second seal is often configured with a variable diameter orifice to be adaptable to various sizes and geometries associated with the instrument shafts. A septum seal, for example is a generally flat, elastomeric member having an expandable orifice therethrough. The orifice may be sized such that the smallest instrument may not pass through the septum seal without engaging and forming a seal with the elastic material. The elasticity of the septum seal permits the orifice to expand to accommodate the largest instrument.

An aspect of concern in the use of such a septum seal is the contact pressure applied by the septum seal on the instrument shaft. If the contact pressure is insufficient, the insufflation pressure may not be maintained as the surgeon manipulates the instrument. If the contact pressure is too great, however, the surgeon may experience difficulty in advancing and properly controlling the instrument. Because lager instruments must expand the orifice to a greater degree, the contact pressure is consequently larger than for smaller instruments, and thus larger instruments may be more difficult to manipulate than smaller instruments. Accordingly, a need exists for an apparatus for forming a seal about an instrument inserted through a cannula that is capable of accommodating variously sized instruments while ensuring an appropriate contact pressure.

SUMMARY

The present disclosure describes an apparatus for the introduction of surgical instruments to an internal surgical site. The apparatus includes an access member for positioning within body tissue having a longitudinal passageway providing access to a tissue site and defining a longitudinal axis. An elongated seal member is mounted to the access member. The elongated seal member has an orifice with a variable inner dimension therethrough and is adapted to establish a sealing relation about an instrument inserted into the access member. A powered adjustment mechanism is associated with the elongated seal for adjusting the variable inner dimension of the orifice. The powered adjustment mechanism includes a trailing hub and a leading hub longitudinally spaced and mounted to the access member so as to permit relative rotational movement between the hubs about the longitudinal axis. A plurality of spokes extends between and connects the trailing hub to the leading hub. The spokes define a first minimum internal dimension in a first condition thereof and define a second minimum internal dimension in a second condition thereof upon relative rotation of the trailing hub and the leading hub, the first minimum internal dimension being greater than the second minimum internal dimension. The spokes are further arranged about the elongated seal member such that relative rotation of the trailing hub and the leading hub adjusts the variable inner dimension of the orifice. A powered motion generator is operatively associated with at least one of the trailing hub and the leading hub for effecting relative rotation therebetween.

The surgical access apparatus may incorporate an electric motor as the powered motion generator. One of the trailing hub and the leading hub may be fixed with respect to the access member, and the other of the trailing hub and leading hub may be operatively associated with the powered motion generator. The other of the trailing hub and leading hub may be coupled to an electric motor and a gear to transmit rotational motion. The powered adjustment mechanism may also include a powered motion generator adapted for generating longitudinal motion.

The surgical access apparatus may include a sensor adapted to detect the presence of the instrument. The sensor may be operatively associated with control circuitry which is operatively associated with the motor. The control circuitry may have logic adapted for controlling a closure force imparted on the instrument by the elongated seal member. The logic of the control circuitry may be adapted to receive information regarding the size of the instrument to automatically impart a predetermined closure force to the instrument. The control circuitry may be adapted to move the spokes to the first condition in the absence of an instrument. The surgical access may further include a zero-closure valve adapted to seal the passageway in the absence of an instrument

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

Figure 1:
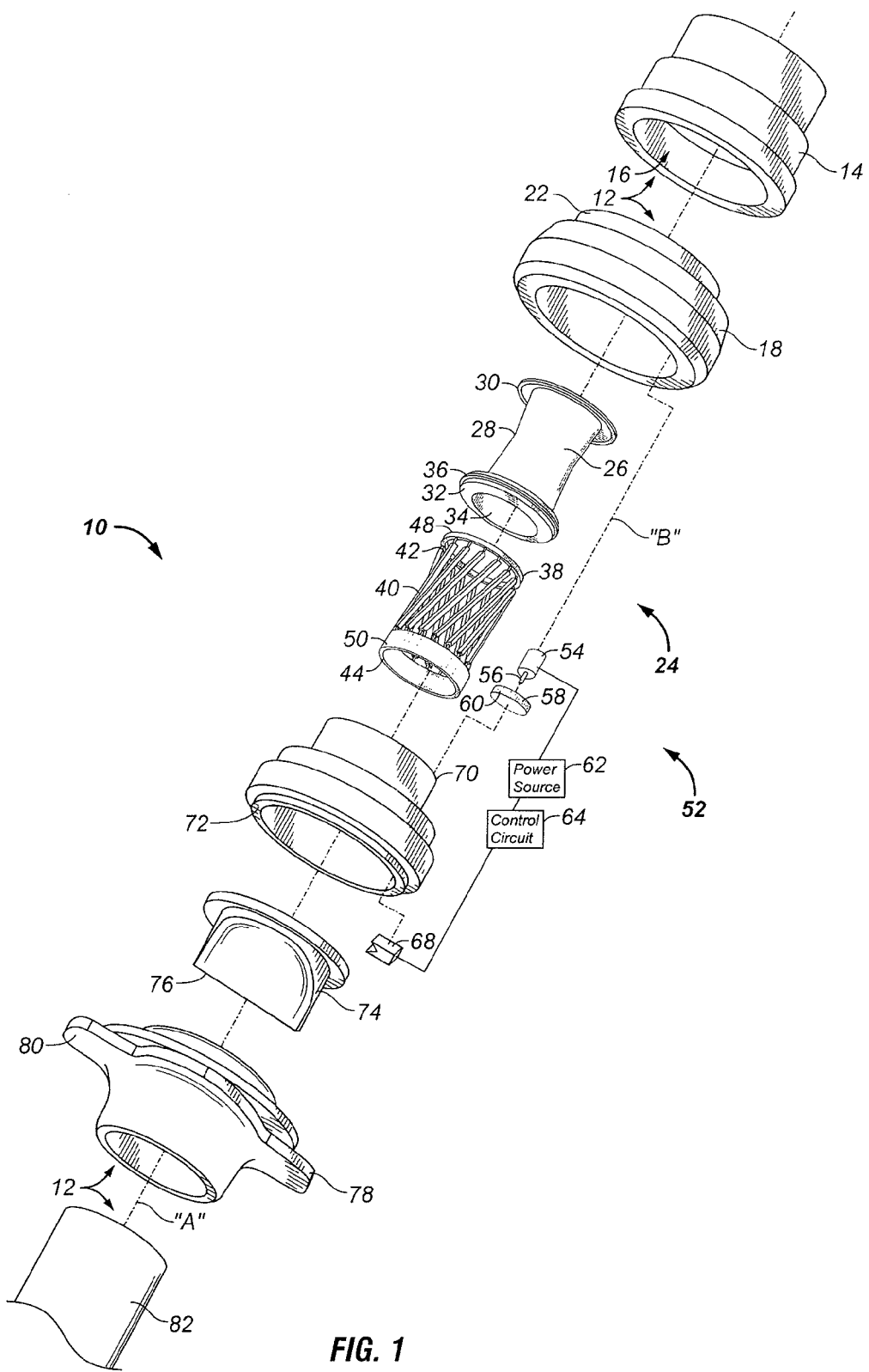
FIG. 1 is an exploded perspective view of an access apparatus constructed in accordance with the present disclosure.

The present disclosure contemplates the introduction into a person's body of all types of surgical instruments including clip appliers, graspers, dissectors, retractors, staplers, laser fibers, photographic devices, endoscopes and laparoscopes, tubes, and the like. All such objects are referred to herein generally as "instruments." In the drawings and in the description which follows, the term "proximal," as is traditional, will refer to the direction toward the operator or a relative position on an apparatus which is closer to an operator, while the term "distal" will refer to the direction away from the operator or a relative position on the apparatus which is further from the operator.

The present disclosure contemplates the use of a variable diameter seal incorporating the structure of an ancient winepress mechanism to accommodate instruments of varying diameter. Briefly, a winepress mechanism combines rotational motion with the principals of a toggle-action mechanism to generate a mechanical advantage. A winepress mechanism may include a plurality of spokes connected by hinges at each end of two coaxial plates mounted for relative rotation. As the plates are rotated, the spokes pivot at the hinges altering the distance between the midpoints of the spokes. If a sleeve of a flexible material were draped between the spokes, the adjustable distance between the spokes' midpoints could define the diameter of an adjustable instrument seal. A more comprehensive explanation of a winepress mechanism used in this manner may be found in U.S. Provisional Application 60/931,935 the entire content of which is incorporated herein by reference.

Referring initially to FIG. 1, a surgical portal apparatus in accordance with the present disclosure is depicted generally as 10. Surgical portal apparatus 10 defines a passageway 12 therethrough to permit the introduction of a surgical instrument to a surgical site. At the proximal end, a cap 14 is open to provide an entryway for the instrument. The interior of cap 14 includes a central opening 16, which extends through cap 14 and encompasses a central longitudinal axis "A." Central longitudinal axis "A" may be defined by cannula 82 (discussed below) and may extend centrally through the surgical portal apparatus 10. Adjacent cap 12 is a proximal housing 18, which is also hollow and open at both ends. An annular ridge 22 protrudes from proximal housing 18 to provide for a fluid tight interface with cap 14.

Winepress seal 24 is adapted to reside at least partially within the passageway 12 of portal apparatus 10 to provide a variable diameter sealing mechanism for forming a fluid tight seal with the various instruments that might be inserted. A flexible elastomeric cone 26 is provided as a component of winepress seal 24 to engage the instrument to form a fluid tight seal with the shaft. Elastomeric cone 26 includes a central throat portion 28 and first and second collars 30, 32 at the proximal and distal ends respectively. Elastomeric cone 26 is bowed inward near the central throat portion 28 to give it an hourglass shape. An orifice 34 through the interior of elastomeric cone 26 has a minimum inner orifice dimension "O" (see FIG. 4A) near the central throat portion 28. As discussed below, the minimum inner orifice dimension "O" may be adjusted to a reduced dimension "o" (see FIG. 4B) by modifying the hourglass shape of the elastomeric cone 26. This modification permits winepress seal 24 to adapt to the variously sized instruments. First and second collars 30, 32 protrude radially outward from the central throat portion at the extents of elastomeric cone 26. First collar 30 is adapted to remain stationary within the passageway 12, and may be affixed to an interior surface of cap 14 with an adhesive or other means. Second collar 32 is adapted for both rotational and longitudinal motion with respect to the first collar 30. A bead 36 on second collar 32 may act as a wiper seal with the interior surfaces of the passageway 12 as second collar 32 translates longitudinally such that insufflation gasses do not escape around the elastomeric cone 26.

Spoke tube 38 may be positioned radially around the central throat portion 28 and longitudinally between the collars 30, 32 of elstomeric cone 26 to modify the minimum inner orifice dimension "O." Spoke tube 38 includes an array of relatively rigid spokes 40, connected by hinges 42 to a leading hub 44 and trailing hub 48. The two hubs 44, 48 may each abut a respective one of the first and second collars 30, 32 of elastomeric cone 26. The trailing hub 48 may be securely affixed to first collar 30 such that it remains stationary within passageway 12, while the leading hub 44 may abut second collar 32 such that it may translate with second collar 32 and remain free to rotate relative to second collar 32. The leading hub 44 may be equipped with a series of teeth, protrusions or depressions on an exterior peripheral surface 50 thereof that may be engaged to cause relative rotation of the leading hub 44 with respect to the trailing hub 48. Such relative rotation may permit spokes 40 to pivot about hinges 42. Hinges 42 may be living hinges, e.g. a thinner portion of material that will have the flexibility to permit spokes 40 to pivot about multiple axes simultaneously. A ball and socket joint may also permit the complex motion required of spokes 40. Spoke tube 38 may be formed from a moldable polymeric material such as polypropelene, or other materials may be selected for a particular application.

Winepress seal 24 also includes a powered adjustment mechanism 52 to allow the seal to adapt to differently sized instruments. Powered adjustment mechanism 52 may include a miniature electric motor 54 having a motor shaft 56 and a gear 58 coupled to the motor shaft 56. Gear 58 may include cogs on its outer radial surface 60 that interface with the teeth on the exterior peripheral surface 50 of leading hub 44 such that rotational motion may be transmitted from the motor shaft 56 to the leading hub 44. As depicted, powered adjustment mechanism lies along an axis "B" parallel to axis "A," but other arrangements are contemplated, which may facilitate creation an appropriate gear ratio.

Powered adjustment mechanism 52 may include a power source 62 and control circuit 64 for powering and controlling motor 54. Power source 62 and control circuit 64 may be in electrical communication with one another as well as with motor 54. Power source 62 and control circuit 64 may be housed internally within surgical portal apparatus 10 or positioned remotely depending on the availability of space and other design considerations. An internal position may be preferred. Control circuit 64 may include logic adapted to accept inputs from the motor 54 such as information regarding the rotational position of shaft 56 or the torque applied by the motor 54. A sensor 68 may be adapted to provide additional input for control circuit 64. Sensor 68 may comprise a proximity sensor, optical sensor or other device to detect the presence of an instrument within passageway 12.

Sensor 68 may be positioned within seal support 70, which is captured by proximal housing 18. Seal support 70 includes a circumferential ridge 72 on a distal surface thereof to provide a seat for a zero-closure valve such as duckbill valve 74. Duckbill valve 74 is an elastomeric member with a pair of distally extending substantially flat lips 76 which are normally biased to contact one another to create a substantially fluid-tight seal through the portal apparatus 10 in the absence of an instrument. Lips 76 may be easily separated upon the insertion of an instrument from the proximal side to permit passage of the instrument. The use of other types of zero-closure valves is also contemplated.

Distal housing 78 encloses duckbill valve 74 and forms a fluid-tight connection with proximal housing 18 enclosing winepress seal 24 therebetween. On the exterior of distal housing 78, diametrically opposed extensions 80 provide a surface for a surgeon or operator to grip the portal apparatus 10 with two fingers. Distal housing 78 receives an access member such as cannula 82 and forms a fluid-tight interface therewith. Cannula 82 is a hollow tube open at both ends providing a conduit for an instrument through a small incision made in a patient. A distal end (not shown) of cannula 84 may be positioned in a body cavity adjacent a tissue site, while the proximal end coupled to distal housing 78 remains external to the patient. Passageway 12 extends through entire portal apparatus 10 from a proximal end of cap 14 to the distal end of cannula 84 to provide access for a surgical instrument to a body cavity.

Figure 2A:
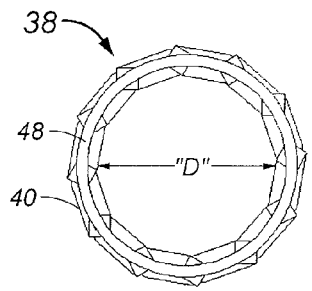
FIG. 2A is a top view of the spoke tube the access apparatus of FIG. 1 arranged in a first open condition for receipt of an instrument.
Figure 3A:
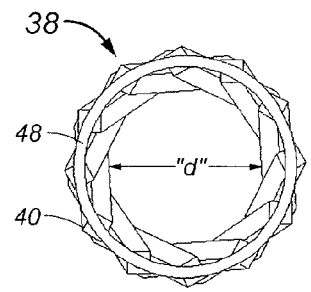
FIG. 3A is a top view of the spoke tube of the access apparatus FIG. 1 arranged in a second closed condition for imparting a closure force to the instrument.
Figure 2B:
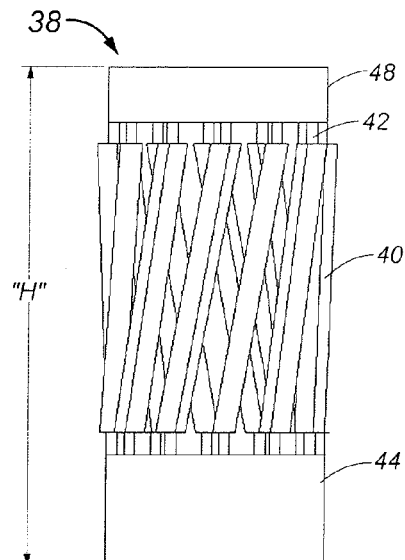
FIG. 2B is a side view of the spoke tube of FIG. 2A.
Figure 3B:
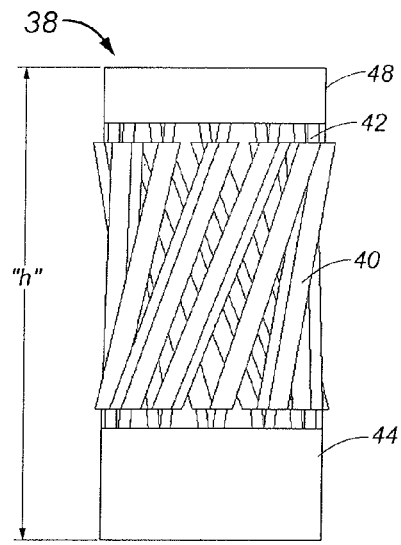
FIG. 3B is a side view of the spoke tube of FIG. 3A.

Referring now to FIGS. 2A and 2B, spoke tube 38 is shown in a first open configuration. Arranged in this manner, spoke tube has an overall height "H" extending from the leading hub 44 to the trailing hub 48 and a minimum inner diameter "D" defined between the midpoints of spokes 40. If the leading hub 44 and trailing hub 48 are caused to rotate relative to one another, spoke tube 38 is rearranged from the first open configuration of FIGS. 2A and 2B to a second closed configuration depicted in FIGS. 3A and 3B. Spokes 40 pivot at hinges 42 such that each spoke 40 leans longitudinally toward the hubs 44, 48 reducing the height to "h." Also, as the spoke tube is moved from the first open configuration to the second closed configuration, the midpoints of the spokes 38 congregate radially to reduce the minimum inner diameter to a dimension "d." Aligning the midpoints of the spokes 40 with the central throat portion 28 allows the midpoints of the spokes 40 to impart a pressure on the flexible elastomeric cone 26 to influence the orifice dimension "O" in order to accommodate instruments of various sizes.

Figure 4A:
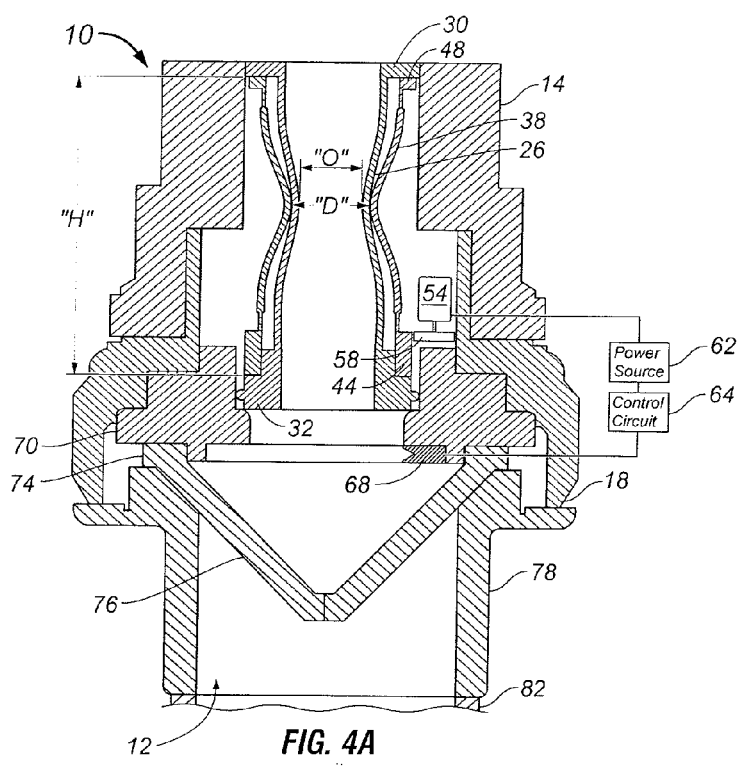
FIG. 4A is a cross-sectional view of the access apparatus of FIG. 1 taken along a plane through central longitudinal axis "A"

Referring now to FIG. 4A, portal apparatus 10 may be assembled such that passageway 12 is sealed in the absence of an instrument by duckbill valve 74 or another zero-closure valve. The lips 76 are biased to contact one another to close passageway 12. Also in the absence of an instrument, spoke tube 38 may be configured to assume its first open configuration with height "H" and inner diameter "D." This arrangement allows elastomeric cone 26 to provide an orifice dimension "O." In this arrangement, the distal most surface of second collar 32 of elastomeric cone 26 abuts a proximally facing surface of the surface of seal support 70 while a proximal most portion of elastomeric cone is fixedly attached to cap 14. Outer radial surface 60 of gear 58 interfaces with a proximal portion of the exterior peripheral surface 50 of leading hub 44. In this arrangement, surgical portal apparatus 10 is in a condition for receiving an instrument.

Figure 4B:
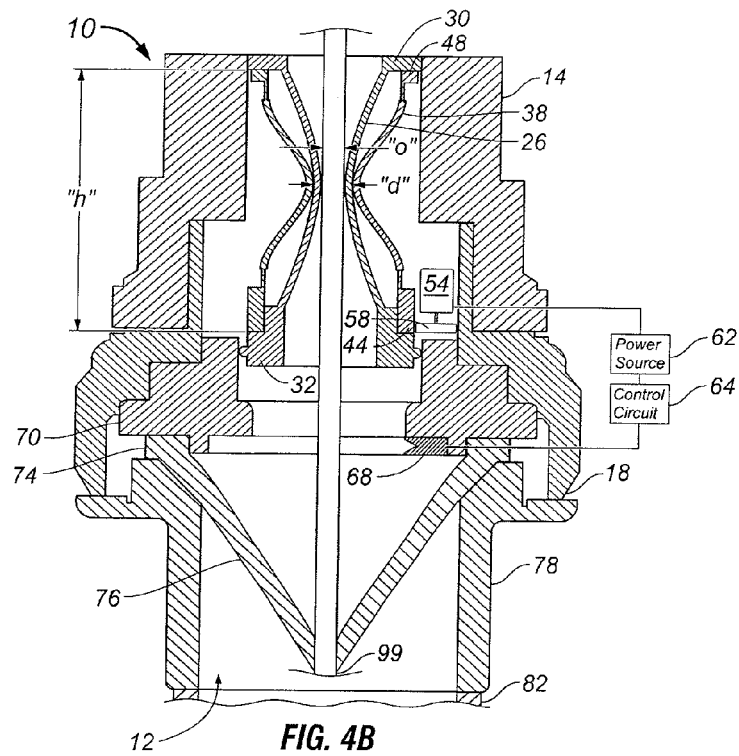
FIG. 4B is a view similar to FIG. 4A depicting the access apparatus in receipt of an instrument.

Referring now to FIG. 4B, an instrument shaft 99 may enter passageway 12 from a proximal side of cap 12 moving in a distal direction. The hourglass shape of the elstomeric cone 26 provides a generous lead in angle facilitating the introduction of the instrument shaft 99. As the instrument shaft 99 moves through seal support 70 it may be detected by sensor 68. Sensor 68 may send a signal to control circuit 64 which may then provide instructions to motor 54. Motor 54 may cause gear 58 to rotate leading hub 44 in a direction causing the leading hub 44 to translate in a proximal direction until spoke tube 38 assumes a height "h." The midpoints of spokes 40 may congregate, pressing radially inwardly on elastomeric cone 26 until second collar 32 no longer contacts the proximally facing surface of the surface of seal support 70. Elastomeric cone 26 is thus configured to provide a reduced orifice dimension "o" to accommodate the particular size of instrument shaft 99.

Control circuit 64 may include components necessary to monitor the closure force applied by the elastomeric cone 26 to the instrument shaft 99. The closure force may be determined indirectly by monitoring a current draw by motor 54 or another characteristic of motor operation. In this way a closure force sufficient to maintain pneumoperitoneum may be achieved, but not so great a closure force as to make manipulations of the instrument shaft 99, e.g., insertion and extraction, awkward for a surgeon or operator. By using the control circuit 64 and motor 54 to control this closure force, an appropriate closure force may be achieved automatically regardless of the size of instrument inserted. While in use, the gearing of the motor 54 will prevent radial forces imparted by the instrument from dilating the orifice.

When the surgeon completes a procedure, the instrument shaft 99 may be withdrawn in a proximal direction. As the instrument passes through seal support 70, sensor 68 may detect the withdrawal of the instrument and send an appropriate signal to control circuit 64. Control circuit 64 may instruct motor 54 to return spoke tube 38 to the first open condition thereof. Returning the spoke tube 38 to the first open condition adjusts the orifice dimension "O" which may facilitate further withdrawal of the instrument, particularly when a specimen is removed from the tissue site through the portal apparatus 10. In this way, surgical portal apparatus 10 may automatically adapt to seal variously sized instruments without input from the operator.

Other arrangements of the various components described above are also contemplated. For example, in contrast to electric motor 54, the powered motion generator may be adapted to generate longitudinal rather than rotational motion. A hydraulic piston (not shown) may be adapted to adjust the longitudinal spacing of the between the leading hub 44 and the trailing hub 48. Because of the hinged arrangement of the spokes 40, relative rotation of the hubs 44, 48 will accompany the longitudinal adjustment and the variable orifice dimension "O" may thus be adjusted.

Surgical portal apparatus 10 is adapted for automatic adjustment, but may alternatively or additionally include a user interface (not shown) for manual control. Manual controls may function, for example, to facilitate unanticipated conditions or to accommodate individual preferences of the surgeon or operator.

Although the foregoing disclosure has been described in some detail by way of illustration and example, for purposes of clarity or understanding, it will be obvious that certain changes and modifications may be practiced within the scope of the appended claims.

What is claimed is:

1. A surgical access apparatus, which comprises:
    an access member dimensioned for positioning within body tissue and defining a longitudinal axis, the access member having a longitudinal passageway therethrough providing access to a tissue site;
    an elongated seal member mounted to the access member, the elongated seal member having an orifice therethrough, the orifice having a variable inner dimension adapted to establish a sealing relation about an instrument inserted into the access member; and
    a powered adjustment mechanism associated with the elongated seal for adjusting the variable inner dimension of the orifice, the powered adjustment mechanism comprising:
        a trailing hub and a leading hub mounted to the access member, the trailing hub longitudinally spaced from the leading hub, the trailing hub and the leading hub adapted for relative rotational movement therebetween about the longitudinal axis;
        a plurality of spokes extending between and connected to the trailing hub and the leading hub, the spokes defining a first minimum internal dimension in a first condition thereof and defining a second minimum internal dimension in a second condition thereof upon relative rotation of the trailing hub and the leading hub, the first minimum internal dimension being greater than the second minimum internal dimension, the spokes further arranged about the elongated seal member such that relative rotation of the trailing hub and the leading hub adjusts the variable inner dimension of the orifice; and
        a powered motion generator operatively associated with at least one of the trailing hub and the leading hub for effecting relative rotation therebetween.

2. The surgical access apparatus according to claim 1, wherein the powered motion generator includes an electric motor.

3. The surgical access apparatus according to claim 1, wherein one of the trailing hub and the leading hub is fixed with respect to the access member and the other of the trailing hub and leading hub is operatively associated with the powered motion generator.

4. The surgical access apparatus according to claim 3, wherein the powered adjustment mechanism includes a motor and a gear coupled to the other of the trailing hub and leading hub to transmit rotational motion.

5. The surgical access apparatus according to claim 1, wherein the powered adjustment mechanism includes a powered motion generator adapted for generating longitudinal motion.

6. The surgical access apparatus according to claim 1, further comprising a sensor for detecting the presence of the instrument.

7. The surgical access apparatus according to claim 6, further comprising control circuitry operatively associated with the motor and having logic adapted for controlling a closure force imparted on the instrument by the elongated seal member.

8. The surgical access apparatus according to claim 7, wherein the logic of the control circuitry is adapted to receive information regarding the size of the instrument to automatically impart a predetermined closure force to the instrument.

9. The surgical access apparatus according to claim 6, wherein the control circuitry is adapted to move the first condition in the absence of an instrument.

10. The surgical access apparatus according to claim 1, further including a zero-closure valve adapted to seal the passageway in the absence of an instrument.

* * * * *